United States Patent [19]
Weigel

[11] Patent Number: 6,001,994
[45] Date of Patent: Dec. 14, 1999

[54] PROCESS FOR MAKING GEMCITABINE HYDROCHLORIDE

[75] Inventor: John A. Weigel, Lafayette, Ind.

[73] Assignee: Eli Lilly and Company, Indianapolis, Ind.

[21] Appl. No.: 09/209,398

[22] Filed: Dec. 10, 1998

Related U.S. Application Data

[63] Continuation of application No. 09/010,438, Jan. 22, 1998, Pat. No. 5,912,366, which is a continuation of application No. 08/762,622, Dec. 9, 1996, Pat. No. 5,756,775
[60] Provisional application No. 60/008,522, Dec. 13, 1995.
[51] Int. Cl.$^6$ .......................... C07H 19/00; C07C 327/00
[52] U.S. Cl. .................... 536/28.1; 536/22.1; 549/453; 549/454
[58] Field of Search ............................ 549/453; 536/28.1

[56] References Cited

U.S. PATENT DOCUMENTS

| | | |
|---|---|---|
| 4,211,773 | 7/1980 | Lopez et al. . |
| 4,526,988 | 7/1985 | Hertel . |
| 4,965,374 | 10/1990 | Chou et al. . |
| 5,428,176 | 6/1995 | Weigel . |
| 5,436,229 | 7/1995 | Ruterbories et al. . |

FOREIGN PATENT DOCUMENTS

| | | | |
|---|---|---|---|
| 0 122 707 | 10/1984 | European Pat. Off. | ........ C07H 19/04 |
| 0 655 454 | 5/1995 | European Pat. Off. | .......... C07F 7/18 |

OTHER PUBLICATIONS

Schmid, Christopher, et al., *Synthesis*, 6:587–590 (1992).
Hiyama, Tamejiro, et al., *Tetrahedron Letters*, 24(38) : 4113–4116 (1983).
Seyferth, Dietmar, et al., *J. Am. Chem. Soc.*, 105:4634–4639 (1983).
Yang, Zhen–Yu, et al., *J. Org. Chem.*, 56:1037–1041 (1991).
Lang, Robert W., et al., *Tetrahedron Letters*, 29(24) :2943–2946.
Burton, donald J., et al., *J. of Fluorine Chemistry*, 38:125–129 (1988).
Hallinan, E. Ann, et al., *Tetrahedron Letters*, 25(22) : 2301–2302.
Hertel, L.W., et al, *J. Org. Chem.*, 53:2406–2409 (1988).
Chou, T.S., et al., *Synthesis*, 565–570, Jun. 1992.
Kitagawa, Osamu, et al., *Tetrahedron Letters*, 29(15) : 1803–1806 (1988).
Cherest, Marc, et al., *Tetrahedron Letters*, 18:2199–2204 (1968).
Douglas, Kenneth T., *Acc. Chem. Res.*, 19:186–192 (1986).
Kornilov, Andrew M., et al., *Tetrahedron: Asymmetry*, 5(6) : 1015–1018 (1994).
Taguchi, Takeo, et al., *Tetrahedron Letters*, 29(41) : 5291–5294 (1988).
Kitagawa, Osamu, et al., *Tetrahedron Letters*, 29(15) :1803–1806 (1988).
Greuter, Hans, et al., *Tetrahedron Letters*, 29(27) :3291–3294 (1988).
Okano, Takashi, et al., *Tetrahedron Letters*, 33(24) :3491–3494 (1992).
Yan, Zhen–Yu, *J. Org. Chem.*, 57:4676–4683 (1992).
Arnone, Alberto, et al., *J. Org. Chem.*, 59:3459–3466 (1994).
Ichikawa, Junji, et al., *Tetrahedron Letters*, 33(26) :3779–3782 (1992).
Ichikawa, Junji, et al., *Tetrahedron Letters*, 33(3) :337–340 (1992).
Wilkinson, John A., *Chem. Rev.*, 92:505–519 (1992).
Fpercy, Jonahan M., *Tetrahedron Letters*, 31(27) :3931–3932 (1990).
Braun, Manfred, et al., *J. Prakt. Chem.*, 335:653–668 (1993).
Bennett, Andrew J., et al., *Synlett*, 6:483–484 (1992).
York, Chentao, et al., *Synlett*, 6:425–426 (1994).
Hanzawa, Yuji, et al., *Tetrahedron Letters*, 28(6) :659–662 (1987).
Frogier, P.R.T., et al., *Antiviral Chemistry & Chemotherapy*, 5(6) :372–379 (1994).
Chou, T.S., et al., Synthesis, 565–570 Jun. 1992.
Morikawa, Tsutomu, et al., *J. Fluorine Chemistry*, 65:79–89 (1993).
Xu, Ze–Qi, et al., *J. of Fluorine Chemistry*, 58:71–79 (1992).
Matsumura, Yasushi, et al., *J. of Fluorine Chemistry*, 57:203–207 (1992).
Shen, Yanchang, et al., *J. of Fluorine Chemistry*, 67:229–232 (1994).
Anh, Nguyen Trong, et al., *Nouveau J. De Chimie*, 1(1) :61–70 (1976).
Hershfield, Robert, et al., *J. Am. Chem. Soc.*, 95 (12) :3994–4002 (1973).
Wemple J., *Tetrahedron Letters*, 38:3255–3258 (1975).

*Primary Examiner*—Jose' G. Dees
*Assistant Examiner*—Sabiha N. Qazi
*Attorney, Agent, or Firm*—Michael J. Sayles; Brian P. Barrett

[57] ABSTRACT

An improved process to make gemcitabine hydrocrhloride, the improvement consisting essentially of making the lactone intermediate, 2-deoxy-2,2-difluoro-D-erythro-pentafuranose-1 ulose-3,5-dibenzoate:

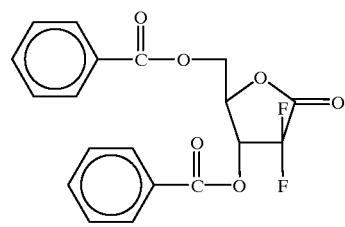

from D-erythro-2-Deoxy-2,2-difluoro 4,5-O-(1-ethylpropyl)-idene) pentoic acid tert Butyl ester wherein, the D-erythro-2-deoxy-2,2 difluoro-4,5-O-(1-ethylproyl)-ideno) pentoic acid tert-Butyl ester is prepared by the process of reacting S-tert-butyl difluoroethane thioate with 2,3-O(1-ethylpropylidene)-D-glyceraldehyde, in a solvent and in the presence of a strong base; with the proviso that the process is conducted in the absence of a catalyst and in the absence of a silyl containing compound.

1 Claim, No Drawings

PROCESS FOR MAKING GEMCITABINE HYDROCHLORIDE

This is a continuation of application Ser. No. 09/010,438, filed Jan. 22, 1998, now U.S. Pat. No. 5,912,366, which is a continuation of application Ser. No. 08/762,622, filed Dec. 9, 1996 (now U.S. Pat. No. 5,756,775).

This application claims the benefit of U.S. Provisional Application No. 60/008,522 filed Dec. 13, 1995.

FIELD OF THE INVENTION

The invention relates to the art of organic chemistry. Specifically it relates to certain α,α-difluoro-β-hydroxy thiol esters and processes to make them.

BACKGROUND OF THE INVENTION

α,α-Difluoro-β-hydroxy thiol esters are useful as intermediates in organic syntheses of valuable pharmaceutical products.

A particularly useful α,α-difluoro-β-hydroxy ester is:

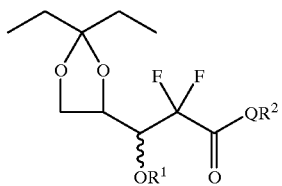

where $R^1$ is selected from the group consisting of H, $C_1$–$C_4$ alkyl, substituted alkyl, including silyl alkyl, trialkyl silyl, aryl, substituted aryl, including silyl aryl, $R^2$ is independently selected from alkyl and aryl groups, and Q is either S (for thiol esters) or O (for esters). Compounds of formula I are known to be useful in the synthesis of gemcitabine hydrochloride (II), a known anti-neoplastic agent.

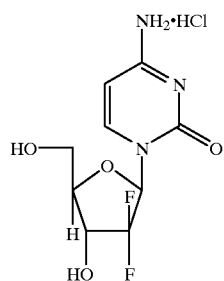

Existing methods to make compounds of formula I where $R^1$ is $SiR^3R^4R^5$, $R^2$ is $R^6$, Q is S, and $R^3$, $R^4$, $R^5$ and $R^6$ are independently selected from $C_1$–$C_4$ alkyl and $C_5$–$C_6$ aryl groups are known in the art. See U.S. Pat. No. 5,428,176. The processes to make compounds of formula (I) as described in the '176 patent require a trialkyl(or triaryl) silylhalide and the use of a catalyst.

Existing methods to make compounds of formula I where $R^1$ is trialkylsilyl, $R^2$ is alkyl and Q is O, are described and claimed in European Patent Application No. 94308806.2 (Publication No. 655454). These methods also require a trialkylsilyl halide and the use of a catalyst.

It is desirable to develop alternate processes that use fewer reagents to make certain α,α-difluoro-β-hydroxy thiol esters, because the use of fewer reagents would lower the overall cost of the synthesis. It is also desirable to synthesize additional α,α-difluoro-β-hydroxy thiol ester compounds which are useful as intermediates in organic syntheses of valuable pharmaceutical products.

SUMMARY OF THE INVENTION

A first aspect of this invention are α,α-Difluoro-β-hydroxy thiol esters of formula (III)

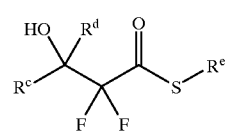

wherein:
$R^c$ and $R^d$ are independently selected from the group consisting of H, $C_1$–$C_6$ alkyl, substituted $C_1$–$C_6$ alkyl, S-tert-butyl difluorothioacet-2-yl, $C_3$–$C_8$ cycloalkyl, $C_3$–$C_8$ cycloalkenyl, substituted $C_3$–$C_8$ cycloalkyl, substituted $C_3$–$C_8$ cycloalkenyl, aryl, substituted aryl, $C_6$–$C_{10}$ fused automatic rings, and substituted $C_6$–$C_{10}$ fused aromatic rings; or
$R^c$ and $R^d$ together make up a ring selected from the group consisting of $C_3$–$C_8$ cycloalkyl, $C_3$–$C_8$ cycloalkenyl, substituted $C_3$–$C_8$ cycloalkyl and substituted $C_3$–$C_8$ cycloalkenyl;
$R^e$ is selected from the group consisting of $C_1$–$C_{10}$ alkyl, substituted $C_1$–$C_{10}$ alkyl, aryl, substituted aryl, $C_3$–$C_8$ cycloalkyl, $C_3$–$C_8$ cycloalkenyl, substituted $C_3$–$C_8$ cycloalkyl and substituted $C_3$–$C_8$ cycloalkenyl, $C_6$–$C_{10}$ fused aromatic rings, and substituted $C_6$–$C_{10}$ fused aromatic rings.

A second aspect of this invention is a difluoroethanethioate compound of formula (IV):

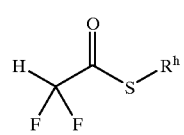

wherein $R^h$ is selected from the group consisting of $C_3$–$C_8$ cycloalkenyl and substituted $C_3$–$C_8$ cycloalkenyl.

A third aspect of this invention is a process to make α,α-difluoro-β-hydroxy thiol esters of formula (IIIA),

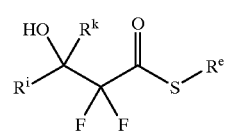

wherein:
$R^i$ and $R^k$ are independently selected from the group consisting of H, $C_1$–$C_6$ alkyl, substituted $C_1$–$C_6$ alkyl, S-tert-butyl difluorothioacet-2-yl, $C_3$–$C_8$ cycloalkyl, $C_3$–$C_8$ cycloalkenyl, substituted $C_3$–$C_8$ cycloalkyl, substituted $C_3$–$C_8$ cycloalkenyl, aryl, substituted aryl, 1,3-dioxolan-4-yl, substituted 1,3-dioxolan-4-yl, $C_6$–$C_{10}$ fused aromatic rings, substituted $C_6$–$C_{10}$ fused aromatic rings; or $R^i$ and $R^k$ together make up a ring selected from the group consisting of $C_3$–$C_8$ cycloalkyl, $c_3$–$C_8$ cycloalkenyl, substituted $C_3$–$C_8$ cycloalkyl, and substituted $C_3$–$C_8$ cycloalkenyl;

$R^e$ is selected from the group consisting of $C_1$–$C_{10}$ alkyl, substituted $C_1$–$C_{10}$ alkyl, aryl, substituted aryl, $C_3$–$C_8$ cycloalkyl, $C_3$–$C_8$ cycloalkenyl, substituted $C_3$–$C_8$ cycloalkyl, and substituted $C_6$–$C_{10}$ cycloalkenyl, $C_6$–$C_{10}$ fused aromatic rings, and substituted $C_6$–$C_{10}$ fused aromatic rings; comprising reacting a difluoroethanethioate of formula (IVA)

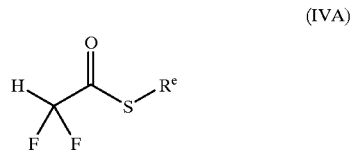

(IVA)

wherein $R^e$ is as defined previously;

with a second reactant selected from the group consisting of aldehydes, ketones, acid halides and esters; in a solvent and in the presence of a strong base; with the proviso that the process is conducted in the absence of a catalyst and in the absence of a silyl containing compound.

A fourth aspect of this invention is a process to make gemcitabine hydrochloride, the improvement consisting essentially of making the lactone intermediate, 2-deoxy-2,2-difluoro-D-erythro-pentofuranose-1-ulose-3,5-dibenzoate:

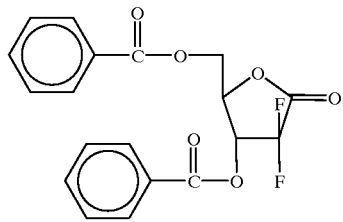

from D-erythro-2-Deoxy-2,2-difluoro-4,5-O-(1-ethylpropylidene) pentoic acid, tert-Butyl thioester, with said D-erythro-2-Deoxy-2,2-difluoro-4,5-O-(1-ethylpropylidene) pentoic acid, tert-Butyl thioester being made by the process of the third aspect of this invention.

DETAILED DESCRIPTION OF THE INVENTION

The following definitions are set forth to illustrate and define the meaning and scope of the various terms used to describe the invention herein.

The term "alkyl" by itself or as part of another substituent means a monovalent compound having the stated number of carbon atoms containing only carbon and hydrogen, and which my be straight or branched chain. The term is exemplified by compounds containing from 1 to 10 carbon atoms, such as, but not limited to, methyl, ethyl, propyl, isopropyl, n-butyl, isobutyl, sec-butyl and tert-butyl (t-butyl), n-pentyl, iso-pentyl, n-hexyl, isohexyl, heptyl, octyl, nonyl and decyl; "$C_1$–$C_4$ alkyl" refers to alkyl compound of from 1–4 carbon atoms. "$C_1$–$C_6$ alkyl" refers to alkyl compounds of from 1–6 carbon atoms. "$C_1$–$C_{10}$" alkyl refers to alkyl compounds of from 1–10 carbon atoms.

The term "substituted" means one to three hydrogens on the structure have been replaced with a like number of moieties independently selected from the group consisting of bromo, chloro, iodo, fluoro, $C_1$–$C_{10}$ alkyl, $C_1$–$C_6$ alkoxy, —COOH, amino or hydroxyl, with the proviso that any substituted structure must be so configured that it is sterically feasible, affords a stable structure and is capable of reacting as described herein.

The term "$C_1$–$C_6$ alkoxy" refers to monovalent structures of the formula —O—($C_1$–$C_6$ alkyl). $C_1$–$C_6$ alkoxy includes, but is not limited to, methoxy(—OCH$_3$), ethoxy-(—OCH$_3$), propoxy(—OCH$_2$CH$_2$CH$_3$), butoxy(—OCH$_2$CH$_2$CH$_2$CH$_3$), pentoxy(—OCH$_2$CH$_2$CH$_2$CH$_2$CH$_3$) and hexoxy(—OCH$_2$CH$_2$CH$_2$CH$_2$CH$_2$CH$_3$).

To be "aromatic" ring must contain one or more groups of atoms in a cyclic array that contains clouds of delocalized π electrons above and below the plane of the atoms; furthermore, the π clouds must contain a total of (4q+2) π electrons, where q is any positive integer.

The term "aryl" refers to:

a monovalent 5 or 6 membered aromatic ring that will afford a stable structure containing all carbon atoms; or containing carbon atoms and: one or two nitrogen atoms; one sulfur atom; one oxygen atom; one nitrogen and one sulfur atom; one oxygen atom and one sulfur atom; or one nitrogen and one oxygen atom. The 5-membered ring has one or two double bonds and the 6-membered ring has two or three double bonds. Examples of aryl structures are:

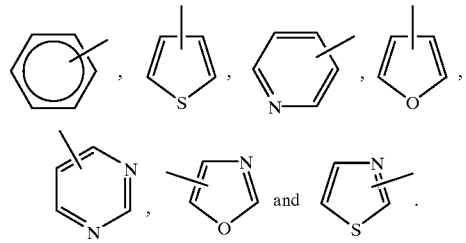

The term "$C_6$–$C_{10}$ fused aromatic rings" refers to two fused aromatic rings that have at least six and at most ten carbon atoms in the rings. Fused aromatic rings are monovalent, with the bond to the rest of the structure being attached to any available ring carbon. Fused aromatic rings are carbocyclic or contain from one to four heteroatoms independently selected from the group consisting of nitrogen, oxygen and sulfur. Fused aromatic rings are configured as follows: when there are six carbon atoms present in the rings, there are at least four heteroatoms in the rings and all of these heteroatoms are nitrogen; when there are seven carbon atoms present in the rings, there are at least three heteroatoms present in the rings, only one of which may be sulfur; when there are eight carbon atoms present in the rings there are at least two heteroatoms, which may be the same or different, present in the rings; when there are nine carbon atoms in the ring, there may or may not be one heteroatom in one of the rings; and when there are ten carbon atoms in the rings there are no heteroatoms in the rings. Examples of some "$C_6$–$C_{10}$ fused aromatic rings" include, but are not limited to, the following structures:

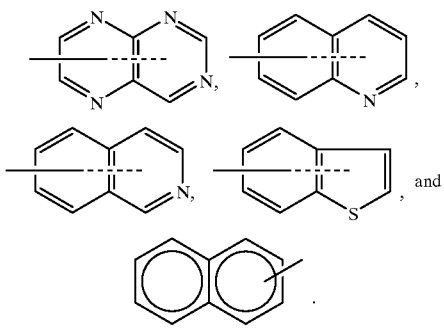

The solid bond that becomes a dotted line bond present in the above structures indicates that the bond can be attached to any available carbon in any ring that the solid-dotted line intersects.

The term "$C_3$–$C_8$ cycloalkyl" refers to saturated carbocyclic ring structures containing from 3 to 8 carbon atoms. Examples of some "$C_3$–$C_8$ cycloalkyl" rings include, cyclopropyl, cyclobutyl, cyclopentyl, cyclohexyl, cycloheptyl and cyclooctyl.

The term "$C_3$–$C_8$ cycloalkenyl" refers to carbocyclic ring structures containing from 3 to 8 carbon atoms and one double bond.

The term "halo" refers to bromo, iodo, fluoro and chloro.

Preferred difluoroethanethioate compounds of formula (IV) are selected from the group consisting of:
S-cyclobuten-3-yl difluoroethanethioate;
S-cyclopenten-1-yl difluoroethanethioate;
S-cyclopenten-3-yl difluoroethanethioate;
S-cyclopenten-4-yl difluoroethanethioate;
S-cyclohexen-1-yl difluoroethanethioate;
S-2-hydroxycyclohexen-3-yl difluoroethanethioate;
S-cyclohexen-4-yl difluoroethanethioate;
S-cyclohepten-1-yl difluoroethanethioate;
S-cyclohepten-3-yl difluoroethanethioate;
S-cyclohepten-4-yl difluoroethanethioate;
S-cyclohepten-5-yl difluoroethanethioate;
S-cycloocten-1-yl difluoroethanethioate;
S-cycloocten-3-yl difluoroethanethioate;
S-cycloocten-4-yl difluoroethanethioate and
S-cycloocten-5-yl difluoroethanethioate.

Preferred α,α-Difluoro-β-hydroxy thiol esters compounds of Formula (III) are selected from the group consisting of:
S-tert Butyl 2,2-Difluoro-3-hydroxy-3-phenylpropanethioate;
S-tert Butyl 2,2-Difluoro-3-hydroxy-3-(4-methoxyphenyl)-propanethioate;
S-tert Butyl 2,2-Difluoro-3-hydroxy-octanethioate;
S-tert Butyl 2,2-Difluoro-3-hydroxy-4,4-dimethylpentanethioate;
S-tert Butyl 2,2-Difluoro-3-hydroxy-4-methylpentanethioate;
S-tert Butyl 2,2-Difluoro-3-hydroxy-3-phenylbutanethioate;
Bis(S-tert Butyl) 2,2,4,4-Tetrafluoro-3-hydroxy-3-phenylpentane-1,5-dithioate;
S-tert Butyl 1-(2-(2,2-difluoroethane-thioate))cyclohex-2-en-1-ol;
D-erythro-2-Deoxy-2,2-difluoro-4,5-O-(1-ethylpropylidene)-pentonic acid, tert-Butyl Thiolester; and
D-threo-2-Deoxy-2,2-difluoro-4,5-O-(1-ethylpropylidene)-pentonic acid, tert-Butyl Thiolester.

The first step in the process of the present invention to make the α,α-difluoro-β-hydroxy thiol esters of the present invention is the synthesis of a difluoroethanethioate of Formula (IVA). A preferred method to synthesize a difluoroethanethioate of Formula (IVA) is as follows:

Step 1. At a temperature of between about 20° C. and about 100° C., under a suitable inert atmosphere such as nitrogen, argon or neon, add difluoroacetic acid or difluoroacetic anhydride dropwise to a solution of chloride containing compound in an aprotic solvent. The chloride containing compound may be any compound that will, under suitable conditions, release chloride to form an acid chloride. Suitable chloride containing compounds include oxaloyl chloride, thionyl chloride, phosgene, phosphorous oxychloride, phosphorous trichloride and phosphorous pentachloride. The preferred chloride containing compound is oxaloyl chloride. Any aprotic solvent may be used; for example: acetonitrile, tetrahydrofuran, dichloromethane, toluene, glyme and xylene are all useful. A preferred aprotic solvent is acetonitrile. The temperature selected depends upon the choice of chloride containing compound and solvent. When oxaloyl chloride in acetonitrile is used, a temperature range for this reaction of about 0° C. to about 80° C. is suitable, with about 25° C. being preferred. From the beginning of the reaction, and at any time thereafter, a catalytic amount of a suitable Lewis acid catalyst may be added. One such suitable Lewis acid catalyst is cobalt (II) chloride. The use of a catalyst in this process is optional.

Step 2. Allow the reactants of step 1 to react from between one and ten hours. The overall reaction time is dependent upon temperature with the higher temperatures having the faster reaction times. Add a sufficient amount of a suitable thiol compound in a dropwise manner, with said suitable thiol compound being of the formula $R^e$—SH, and selected such that the desired $R^e$ component is introduced into the difluoroethanethioate product. For example when $R^e$ is tert-butyl the suitable thiol is 2-methyl-2-propanethiol. A "sufficient amount" is at least one molar equivalent based upon the difluoro starting material.

Step 3. Stir reaction mixture for a sufficient amount of time. A sufficient amount of time could be any time up to 24 hours. Add additional suitable thiol compound, if necessary. The temperature of the reaction mixture can be anywhere between about 20° C. and about 100° C. with 25° C. being the preferred reaction temperature.

Step 4. Perform a standard workup using standard techniques. One such workup is as follows: Pour the reaction mixture over a suitable water immiscible solvent such as diethyl ether ($Et_2O$) and then wash with a suitable basic aqueous solution such as saturated sodium bicarbonate ($NaHCO_3$) in water.

During step 4, the reaction mixture divides into two layers with the desired product contained in the organic layer. The mostly aqueous layer containing the undesired material is separated and discarded in an environmentally sound manner. The layer containing the desired product is dried over a suitable drying reagent such as sodium sulfate ($Na_2SO_4$).

Once the substituted difluoroethanethioate is made it may be kept either at room temperature or, more preferred, kept in a refrigerator at a temperature below 25° C. until it is needed. The substituted difluoroethanethioate (IVA) is used to begin the process to make the α,α-difluoro-β-hydroxy thiol esters (IIIA) of the instant invention. The preferred substituted difluoroethanethioate for the synthesis of gemcitabine hydrochloride is S-tert butyl difluoroethane-thioate.

One synthetic route to α,α-difluoro-β-hydroxy thiol esters is to react a substituted difluoroethanethioate (IV) with a second reactant selected from the group consisting of aldehydes, ketones, acid halides and esters in a solvent and in the presence of a strong base; with the proviso that the process is conducted in the absence of a catalyst and in the absence of a silyl containing compound.

The aldehyde or ketone is of formula (V):

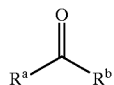

(V)

wherein $R^a$ and $R^b$ are independently selected from the group consisting of H, $C_1$–$C_6$ alkyl, substituted $C_1$–$C_6$ alkyl, $C_3$–$C_8$ cycloalkyl, substituted $C_3$–$C_8$ cycloalkyl, $C_3$–$C_8$ cycloalkenyl, substituted $C_3$–$C_8$ cycloalkenyl, aryl, substituted aryl, 1,3-dioxolan-4-yl, substituted 1,3-dioxolan-4-yl, $C_6$–$C_{10}$ fused aromatic rings and substituted $C_6$–$C_{10}$ fused aromatic rings, or $R^a$ and $R^b$ together make up a ring selected from the group consisting of $C_3$–$C_8$ cycloalkyl, substituted $C_3$–$C_8$ cycloalkyl, $C_3$–$C_8$ cycloalkenyl and substituted $C_3$–$C_8$ cycloalkenyl.

The acid halides are of formula (VI)

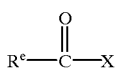

(VI)

where X is Cl, Fl, Br or I and $R^e$ has the same definition as before.

The esters are of formula (VII)

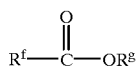

(VII)

where $R^f$ and $R^g$ are independently $R^e$, where $R^e$ has the same definition as before.

Without intending to be a limiting list, examples of suitable aldehydes, ketones, acid halides and esters are as follows.

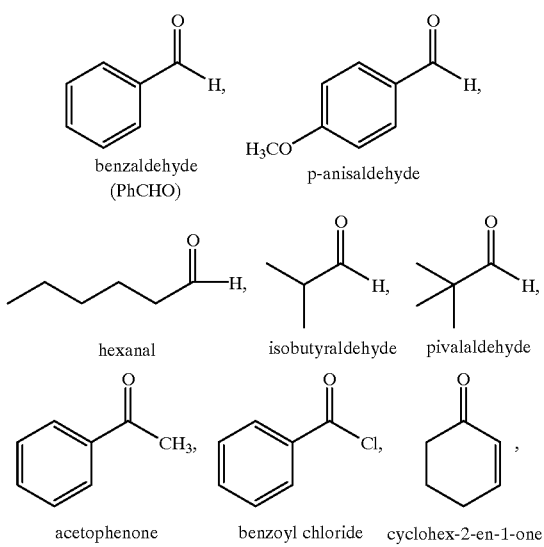

benzaldehyde (PhCHO), p-anisaldehyde, hexanal, isobutyraldehyde, pivalaldehyde, acetophenone, benzoyl chloride, cyclohex-2-en-1-one

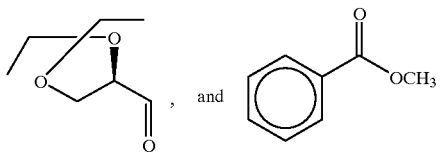

2,3-O-(1-ethyl-propylidene)-D-glyceraldeyde, and methyl benzoate.

Methods to make all of these aldehydes, ketones, acid halides and esters are known in the art of organic chemistry.

The preferred second reactant, for use in the overall synthesis of gemcitabine hydrochloride, is 2,3-O-(1-ethyl-propylidene)-D-glyceraldehyde.

The synthesis involves reacting a difluoroethanethioate (IVA) with a second reactant (of formula V, VI or VII) in a solvent, in the presence of a strong base; with the proviso that the process is conducted in the absence of a catalyst and in the absence of a silyl containing compound.

The preferred order of addition or reagents is to first add the substituted difluoroethanethioate to the solvent, then add the strong base and allow the three components to react for a sufficient length of time before adding the second reactant to the reaction mixture. Of course, this synthesis is preferably conducted under a suitable inert atmosphere such as nitrogen, argon or neon.

Suitable solvents for the synthesis include hydrocarbons, nitrites and ethers. These solvents include, but are not limited to, toluene, xylene, glyme, tetrahydrofuran, acetonitrile, hexane, heptane, diethyl ether and many other solvents of the general class. The most preferred solvent for this reaction is toluene.

The strong base is any suitable strong base such as amides, alkoxides and hydrides. Suitable strong bases include lithium diisopropylamide (LDA), lithium hexamethylsilazide, triethylamine, pyridine and n-butyl lithium. The preferred solvent is LDA.

The sufficient length of time for the substituted difluoroethanethioate, solvent and strong base to react is anywhere between about thirty seconds and about 1 hour. A preferred length of time is about 2 minutes. If desirable, the reaction mixture is capable of being stabilized at this point, preferably by keeping it at a temperature below 25° C., and held indefinitely until needed.

The temperature of the substituted difluoro-ethanethioate/solvent mixture is lowered to between at least about –100° C. and about 25° C. prior to the addition of the strong base. The preferred temperature is about –78° C. After the strong base and the second reactant are added the reaction is allowed to precede at about the same temperature for between about five minutes and about 24 hours.

When the reaction has reached a suitable ending point the reaction mixture may be warmed to about room temperature (about 25° C.). If necessary, the reaction can be quenched by addition of a suitable quenching agent, such as, phosphate buffer. Once the reaction is ended, the organic layer is separated and concentrated under reduced pressure. The crude desired product can be purified by chromatography. The undesired layer can be disposed of in an environmentally sound manner.

This procedure was followed to make the compounds of the claimed invention.

The α,α-difluoro-β-hydroxy thiol esters of the claimed invention are useful as intermediates in organic syntheses of valuable pharmaceutical products.

After D-erythro (a.k.a. anti-) 2-Deoxy-2,2-difluoro-4,5-O-(1-ethylpropylidene) pentoic acid, tert-Butyl thioester is made it can be converted to a lactone of the formula:

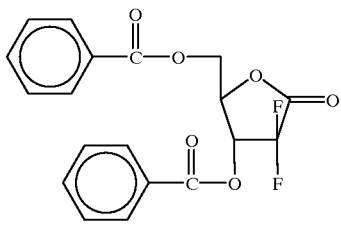

by following the procedures described in U.S. Pat. No. 4,526,988 (columns 7,8) which is incorporated by reference. The lactone is then converted to an alcohol, forming a protected 2-deoxy-2,2-difluororibose compound. This protected 2-deoxy-2,2-difluororibose compound can be reacted with a nucleobase, according to the processes described in European Patent Application No. 93304817.5 (Publication No. 577 303 A1), European Patent Application No. 84301463.0 (Publication No. 122 707), and in European Patent Application No. 88307750.5 (Publication No. 306 190), to form nucleosides, including pharmaceutically acceptable salts of nucleosides, with said nucleosides, and pharmaceutically acceptable salts of said nucleosides, having utility as pharmaceutical products. One such nucleoside is gemcitabine hydrochloride:

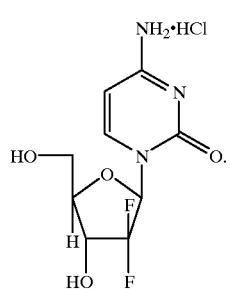

(II)

which is a commercially available (sold under the trademark, GEMZAR® by Eli Lilly and Company, Indianapolis, Ind.) anti-neoplastic drug.

The following examples are illustrative only and are not intended to limit the scope of the invention in any way.

EXAMPLES

The terms and abbreviations used in the instant examples have their normal meanings unless otherwise designated. For example: "° C." refers to degrees Celsius; "N" refers to normal or normality; "mol" refers to mole or moles; "mmol" refers to millimole or millimoles; "g" refers to gram or grams; "mg" refers to milligrams; "ml" refers to milliliter or milliliters; "mp" refers to melting point; "M" refers to molar or molarity; "mm Hg" refers to millimeters of mercury; "Mass spec." refers to mass spectrometry; "IR" refers to infrared spectroscopy; and "NMR" refers to nuclear magnetic resonance spectroscopy.

Unless otherwise noted, all chemicals were reagent grade materials from commercial suppliers and were used without further purification. All reactions were conducted under a nitrogen atmosphere. Melting points are uncorrected. $^1$H NMR spectra were recorded at 300 MHz and were internally referenced to residual CHCl$_3$ (7.24 ppm). $^{13}$C NMR spectra were recorded at 75.5 MHz and were referenced to CHCl$_3$ (77.0 ppm). $^{19}$F NMR spectra were recorded at 282.4 MHz and were referenced to internal C$_6$F$_6$ (−162.9 ppm). Assignments were derived from COSY and H/C correlation spectra and from consideration of the F/C coupling patterns observed in the carbon spectra. IR spectra were recorded as thin films.

Example 1

S-tert Butyl Difluoroethanethioate

To a solution of oxaloyl chloride (9.08 mL, 104 mmol) in acetonitrile (ACN) (50 mL) at 25 ° C. was added dropwise difluoroacetic acid (6.55 mL, 104 mmol). After 3 hours, 2-methyl-2-propanethiol (11.74 mL, 104 mmol) was added dropwise followed by cobalt(II) chloride (10 mg). After being stirred at room temperature for 18 hours, additional 2-methyl-2-propanethiol (4.0 mL, 35.4 mmol) was added. After 2 hours, the solution was poured onto Et$_2$O (500 mL) and washed with saturated NaHCO$_3$ (2×300 mL) and H$_2$O (2×300 mL). The organic layer was dried over Na$_2$SO$_4$, and the solvent was removed under reduced pressure to give a red oil. Vacuum distillation at 30 mm Hg gave S-tert butyl difluoroethane-thioate (8.26 g, 47% yield) as a colorless oil: bp 59–63° C. (30 mm Hg); $^1$H NMR (CDCl$_3$) δ 1.48 (s, 9H), 5.67 (t, 1H, J=54 Hz); $^{13}$C NMR (CDCl$_3$) δ 29.45, 49.32, 108.94 (t, J=255 Hz), 191.23 (t, J=28 Hz); $^{19}$F NMR (CDCl$_3$) δ −123.65 (d, J=55 Hz); IR (film, cm$^{-1}$) 2969, 1684, 1154, 1093, 1064. Anal. Calcd for C$_6$H$_{10}$F$_2$OS: C, 42.84; H, 5.99. Found: C, 43.06; H, 6.15.

Example 2

General Process to Make α,α-difluoro-β-hydroxy thiol esters using S-tert butyl difluoroethanethioate as a starting material To a solution of S-tert butyl difluoroethanethioate (VIII) (0.152 mL, 1.00 mmol) from Example 1 in toluene (10 mL) at −78° C. is added dropwise over 1 min lithium diisopropylamide (0.550 mL of 2.0 M solution in heptane/THF/ethylbenzene, 1.10 mmol). After 2 min, the second reactant (aldehyde (V), ketone (V), acid chloride (VI) or ester (VII) (1.10 mmol)) is added dropwise. After 1 hour, the reaction is warmed to 25° C. over 1 hour and quenched by addition of phosphate buffer (5 mL, 0.5 M, pH=7). The resulting organic layer is concentrated under reduced pressure. The crude product is isolated and purified by chromatography.

Example 3

Synthesis of S-tert Butyl 2,2-Difluoro-3-hydroxy-3-phenylpropanethioate (IX)

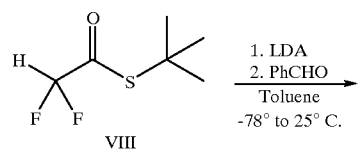

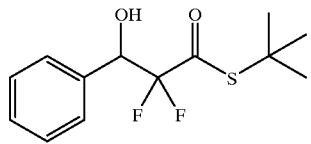

IX

Following the procedure of Example 2, reaction of benzaldehyde (0.112 mL, 1.10 mmol) affords S-tert butyl 2,2-difluoro-3-hydroxy-3-phenylpropanethioate. (IX) (192 mg after isolation and purification, 70% yield) as a colorless oil, which was chromatographed using 10% EtOAc in hexane as eluent: $^1$H NMR (CDCl$_3$) δ 1.46 (s, 9H), 2.52 (br, 1H), 5.16 (dd, 1H), 7.4 (m, 5H); $^{13}$C NMR (CDCl$_3$) δ 29.31, 49.05, 73.49 (t, J=24 Hz), 114.78 (t, J=260 Hz), 127.80, 128.32, 129.10, 134.56, 193.47 (t, J=30 Hz); $^{19}$F NMR (CDCl$_3$) δ −112.88 ($J_{FF}$=259 Hz, $J_{FH}$=9 Hz), −119.22 ($J_{FF}$=259, $J_{FH}$=15 Hz); IR (film, cm$^{-1}$) 3442, 2967, 1673, 1660, 1456, 1367, 1194, 1078, 917.

Example 4

S-tert Butyl 2,2-Difluoro-3-hydroxy-3-(4-methoxyphenyl)-propanethioate (X)

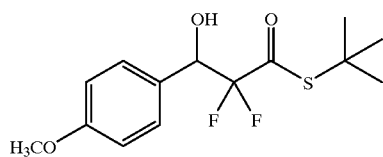

X

Following the procedure of Example 2, reaction of p-anisaldehyde (0.134 mL, 1.10 mmol) affords compound (X) (187 mg after isolation and purification, 62% yield) as a white solid, which was chromatographed using 5% EtOAc in hexane as eluent: mp 73–75° C.; $^1$H NMR (CDCl$_3$) δ 1.45 (s 9H), 2.49 (br, 1H), 3.79 (s, 3H), 5.09 (dd, 1H), 6.87 (d, 2H), 7.31 (d, 2H); $^{13}$C NMR (CDCl$_3$) δ 29.34, 49.04, 55.26, 73.10 (t, J=25 Hz), 113.78, 114.85 (t, J=260 Hz), 126.58, 129.11, 160.19, 193.57 (t, J=31 Hz); $^{19}$F NMR (CDCl$_3$) δ −113.13 ($J_{FF}$=258 Hz, $J_{FH}$=8 Hz), −119.35 ($J_{FF}$=258, $J_{FH}$=15 Hz); IR (film, cm$^{-1}$) 3474, 2960, 1683, 1618, 1519, 1453, 1249, 1177, 1085, 1038, 920.

Example 5

Synthesis of S-tert Butyl 2,2-Difluoro-3-hydroxyoctanethioate (XI)

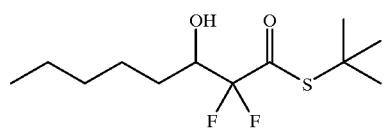

XI

Following the procedure of Example 2, reaction of hexanal (0.132 mL, 1.10 mmol) affords compound (XI) (164 mg after isolation and purification, 61% yield) as a colorless oil, which was chromatographed using 10% EtOAc in hexane as eluent: $^1$H NMR (CDCl$_3$) δ 0.88 (t, 3H), 1.30 (m, 6H), 1.51 (s, 9H), 1.60 (m, 2H), 1.99 (br, 1H), 4.01 (m, 1H); $^{13}$C NMR (CDCl$_3$) δ 13.93, 22.43, 24.88, 29.31, 29.47, 31.41, 49.10, 71.47 (t, J=25 Hz), 115.57 (t, J=259 Hz), 193.55 (t, J=33 Hz); $^{19}$F NMR (CDCl$_3$) δ −114.11 ($J_{FF}$=261 Hz, $J_{FH}$=9 Hz), −119.94 ($J_{FF}$=261, $J_{FH}$=14 Hz); IR (film, cm$^{-1}$) 3450, 2965, 2935, 2859, 1683, 1461, 1367, 1121, 1075.

Example 6

Synthesis of S-tert Butyl 2,2-Difluoro-3-hydroxy-4,4-dimethylpentanethioate (XII)

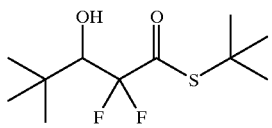

XII

Following the procedure of Example 2, reaction of pivalaldehyde (0.119 mL, 1.10 mmol) affords compound (XII) (107 mg after isolation and purification, 42% yield) as a colorless oil, which was chromatographed using 10% EtOAc in hexane as eluent: $^1$H NMR (CDCl$_3$) δ 1.01 (s, 9H), 1.47 (s, 9H), 2.42 (d, 1H), 3.77 (dt, 1H); $^{13}$C NMR (CDCl$_3$) δ 26.48, 29.36, 34.64, 48.78, 76.76 (t, J=22 Hz), 117.38 (t, J=262 Hz), 194.33 (t, J=30 Hz); $^{19}$F NMR (CDCl$_3$) δ −104.84 ($J_{FF}$=264 Hz, $J_{FH}$=7 Hz), −118.04 ($J_{FF}$=264, $J_{FH}$=20 Hz); IR (film, cm$^{-1}$) 3520, 2960, 1677, 1597, 1460, 1374, 1164, 1064, 854.

Example 7

Synthesis of S-tert Butyl 2,2-Difluoro-3-hydroxy-4-methylpentanethioate (XIII)

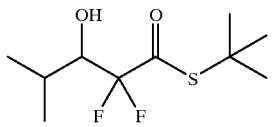

XIII

Following the procedure of Example 2, reaction of isobutyraldehyde (0.100 mL, 1.10 mmol) affords compound (XIII) (105 mg after isolation and purification, 44% yield) as a colorless oil, which was chromatographed using 10% EtOAc in hexane as eluent: $^1$H NMR (CDCl$_3$) δ 0.99 (1, 6H), 1.49 (s, 9H), 1.95 (m, 1H), 2.42 (br, 1H), 3.81 (ddd, 1H); $^{13}$C NMR (CDCl$_3$) δ 16.84, 19.93, 28.44, 29.38, 49.96, 75.01 (t, J=23 Hz), 116.44 (t, J=261 Hz), 193.90 (t, J=30 Hz); $^{19}$F NMR (CDCl$_3$) δ −110.50 ($J_{FF}$=262 Hz, $J_{FH}$=9 Hz), −117.80 ($J_{FF}$=262, $J_{FH}$=17 Hz); IR (film, cm$^{-1}$) 3474, 2967, 1677, 1479, 1466, 1367, 1163, 1064, 893.

Example 8

Synthesis of S-tert Butyl 2,2-Difluoro-3-hydroxy-3-phenylbutanethioate (XIV)

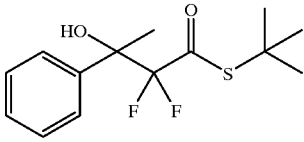

XIV

Following the procedure of Example 2, reaction of acetophenone (0.128 mL, 1.10 mmol) affords compound (XIV) (200 mg after isolation and purification, 69% yield) as a colorless oil, which was chromatographed using 10% EtOAc in hexane as eluent: $^1$H NMR (CDCl$_3$) δ 1.35 (s, 9H), 1.72 (t, 3H), 3.39 (br, 1H), 7.33 (m, 3H), 7.50 (m, 2H); $^{13}$C NMR (CDCl$_3$) δ 23.24 (t, J=3 Hz), 29.10, 49.00, 76.11 (t, J=25 Hz), 114.80 (t, J=265 Hz), 126.33, 128.04, 128.09, 139.49, 194.66 (t, J=32 Hz); $^{19}$F NMR (CDCl$_3$) δ −114.26, −114.91 (J$_{FF}$=259); IR (film, cm$^-$) 3506, 2966, 1676, 1446, 1367, 1120, 1053, 884.

Example 9

Synthesis of Bis(S-tert Butyl) 2,2,4,4-Tetrafluoro-3-hydroxy-3-phenylpentane-1,5-dithioate (XV)

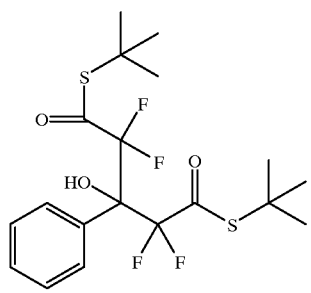

XV

Following the procedure of Example 2, reaction of benzoyl chloride (0.128 mL, 1.10 mmol) affords compound (XV) (170 mg after isolation and purification, 77% yield) as a white solid, which was chromatographed using 10% EtOAc in hexane as eluent: mp 80° C.; $^1$H NMR (CDCl$_3$) δ 1.35 (s,18H), 4.84 (br, 1H), 7.35 (m, 3H), 7.67 (m, 2H); $^{13}$C NMR (CDCl$_3$) δ 29.14, 49.43, 78.75 (t, J=23 Hz), 113.44 (t, J=271 Hz), 127.84, 127.93, 129.42, 131.35, 192.48 (t, J=31 Hz); $^{19}$F NMR (CDCl$_3$) δ −109.93, −110.16 (J$_{FF}$=261); IR (film, cm$^{-1}$) 3473, 2960, 1697, 1657, 1466, 1374, 1143, 966.

Example 10

Synthesis of S-tert Butyl 1-(2-(2,2-difluoroethanethioate))cyclohex-2-en-1-ol (XVI)

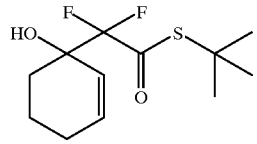

XVI

Following the procedure of Example 2, reaction of cyclohex-2-en-1-one (0.106 mL, 1.10 mmol) affords compound (XVI) (173 mg after isolation and purification, 65% yield) as a colorless oil, which was chromatographed using 15–20% EtOAc in hexane as eluent: $^1$H NMR (CDCl$_3$) δ 1.50 (s, 9H), 1.72 (m, 1H), 1.80 (m, 1H), 2.03 (m, 1H), 2.31 (br, 1H), 5.77 (d, 1H), 6.10 (ddd, 1H); $^{13}$C NMR (CDCl$_3$) δ 17.42, 24.82, 29.48, 29.53, 49.12, 71.64 (t, J=26 Hz), 115.98 (t, J=263 Hz), 123.67, 135.39, 193.81 (t, J=30 Hz); $^{19}$F NMR (CDCl$_3$) δ −115.76, −116.72 (J$_{FF}$=257); IR (film, cm$^{-1}$) 3447, 2960, 2874, 1683, 1460, 1368, 1085.

Example 11

Synthesis of D-ezythro- and D-threo-2-Deoxy-2,2-difluoro-4,5-O-(1-ethylpropylidene)pentonic acid, tert-Butyl Thiolester (XVII, XVIII)

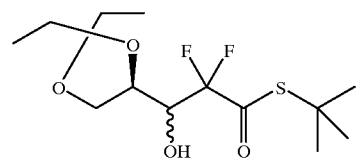

XVII/XVIII   Anti/Syn = 85/15

2,3-O-(3-pentylidene)-D-glyceraldehyde was synthesized by the procedure published in "2,3-O-(3-Pentylidene)-D-glyceraldehyde and 2,3-O-(3-Pentylidene)-L-glyceraldehyde: Convenient Glyceraldehyde Surrogates Obtained via a Novel Periodate-Based Oxidation System", Schmid, C. R.: Bradley, D. A., *Synthesis*, 1992, 587–590.

Following the procedure of Example 2, reaction of 2,3-O-(1-ethylpropylidene)-D-glyceraldehyde (0.155 mL, 1.00 mmol) affords a mixture of compounds XVII and XVIII. Chromatography of the residue with 5% and then 20% EtOAc/hexane as eluents gave erytho-XVII (172 mg, 53% yield) and threo-XVIII (37 mg, 11% yield) as colorless oils.

Data for erythro-XVII: This compound was crystallized from hexane, mp 39–40° C.; $^1$H NMR (CDCl$_3$) δ 0.87 (s, 6H), 1.50 (s, 9H), 1.60 (q, 2H), 1.62 (q, 2H), 2.47 (d, 1H), 3.96 (m, 1H), 4.06 (m, 1H), 4.23 (m, 1H), 4.32 (m, 1H); $^{13}$C NMR (CDCl$_3$) δ 7.90, 8.01, 28.94, 29.28, 29.40, 49.07, 65.45 (t, J=3.8 Hz), 71.05 (t, J=23 Hz), 73.56, 113.19, 115.21 (t, J=260), 192.35 (t, J=31 Hz); $^{19}$F NMR (CDCl$_3$) δ −115.3 (J$_{FF}$=263 Hz, J$_{FH}$=10 Hz), −117.5 (J$_{FF}$=263 Hz, J$_{FH}$=15 Hz); IR (film, cm$^{-1}$) 3427, 2973, 1683, 1460, 1209, 1177, 1137, 1078.

Data for threo-XVIII: $^1$H NMR (CDCl$_3$) δ 0.88 (t, 3H), 0.89 (t, 3H), 1.50 (s, 9H), 1.63 (q, 2H), 1.66 (q, 2H), 2.90 (d, 1H), 3.81 (m, 1H), 3.94 (m, 1H), 4.10 (m, 1H), 4.31 (m, 1H) ; $^{13}$C NMR (CDCl$_3$) δ 7.97, 8.04, 29.02, 29.40, 29.52, 49.15, 66.53, 70.55 (J=25 Hz), 72.36, 114.02, 114.7 (J=263 Hz), 192.58 (J=29 Hz); $^{19}$F NMR (CDCl$_3$) δ −108.78 (J$_{FF}$=267 Hz, J$_{FH}$=6 Hz), −120.01 (J$_{FF}$=267, J$_{FH}$=16 Hz); IR (film, cm$^-$) 3533, 3453, 2973, 1677, 1453, 1170, 1137, 1084.

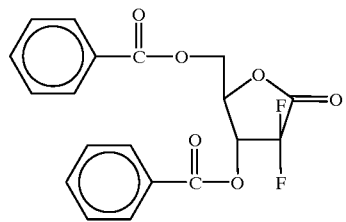

What is claimed is:

1. An improved process to make gemcitabine hydrochloride, the improvement consisting essentially of making the lactone intermediate, 2-deoxy-2,2-difluoro-D-erythro-pentafuranose-1-ulose-3,5-dibenzoate: from D-erythro-2-Deoxy-2,2-difluoro-4,5-O-(1-ethylpropyl)-idene) pentoic acid tert-Butyl ester wherein, the D-erythro-2-Deoxy-2,2-difluoro-4,5-O-(1-ethylpropyl)-idene) pentoic acid tert-Butyl ester is prepared by the process of reacting S-tert-butyl difluoroethane thioate with 2,3-O (1-ethylpropylidene)-D-glyceraldehyde, in a solvent and in the presence of a strong base; with the proviso that the process is conducted in the absence of a catalyst and in the absence of a silyl containing compound.

* * * * *